United States Patent
Saalbach et al.

(10) Patent No.: US 10,417,765 B2
(45) Date of Patent: Sep. 17, 2019

(54) ADAPTIVE SEGMENTATION FOR ROTATIONAL C-ARM COMPUTED TOMOGRAPHY WITH A REDUCED ANGULAR RANGE

(71) Applicant: KONINKLIJKE PHILIPS N.V., Eindhoven (NL)

(72) Inventors: Axel Saalbach, Hamburg (DE); Pieter Gerben Eshuis, Best (NL); Wilhelmus Henrica Gerarda Maria Van Den Boomen, Valkenswaard (NL); Dirk Schäfer, Hamburg (DE); Juergen Weese, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/542,777

(22) PCT Filed: Jan. 6, 2016

(86) PCT No.: PCT/EP2016/050131
§ 371 (c)(1),
(2) Date: Jul. 11, 2017

(87) PCT Pub. No.: WO2016/113161
PCT Pub. Date: Jul. 21, 2016

(65) Prior Publication Data
US 2017/0365059 A1    Dec. 21, 2017

(30) Foreign Application Priority Data
Jan. 14, 2015    (EP) .................................... 15151099

(51) Int. Cl.
*G06T 7/10*    (2017.01)
*A61B 6/00*    (2006.01)
*A61B 6/03*    (2006.01)

(52) U.S. Cl.
CPC ................ *G06T 7/10* (2017.01); *A61B 6/032* (2013.01); *A61B 6/4441* (2013.01); *A61B 6/503* (2013.01);
(Continued)

(58) Field of Classification Search
CPC ....... A61B 6/032; A61B 6/4441; A61B 6/503; A61B 6/504; A61B 6/5205; A61B 6/5258;
(Continued)

(56) References Cited

U.S. PATENT DOCUMENTS 7,734,009 B2    6/2010    Brunner
8,111,894 B2    2/2012    Van De Haar
(Continued)

FOREIGN PATENT DOCUMENTS

EP    2485646 B1    11/2013
WO    2008001260 A2    1/2008

OTHER PUBLICATIONS

Schäfer, D et al Limited angle C-arm tomography and segmentation for guidance of atrial fibrillation ablation procedures, MICCAI, 2012, 634-641.
(Continued)

*Primary Examiner* — Katrina R Fujita

(57) ABSTRACT

The present invention relates to a system (1) for adaptive segmentation. The system (1) comprises a configurator (10), which is configured to determine an adapted angular range (AR) with respect to an operation mode of the system (1) and which is configured to determine a segmentation parameter (SP) based on the adapted angular range (AR). Further, the system comprises an imaging sensor (20), which is configured to acquire images ($I_1, \ldots, I_N$) within the adapted angular range (AR). Still further, the system comprises a segmentator (30), which is configured to generate a segmen-
(Continued)

tation model based on the acquired images ($I_1, \ldots, I_N$) using the determined segmentation parameter (SP).

15 Claims, 4 Drawing Sheets

(52) U.S. Cl.
CPC ............ *A61B 6/504* (2013.01); *A61B 6/5205* (2013.01); *A61B 6/5258* (2013.01); *G06T 2200/24* (2013.01); *G06T 2207/10081* (2013.01); *G06T 2207/10116* (2013.01); *G06T 2207/20092* (2013.01); *G06T 2207/30004* (2013.01)

(58) Field of Classification Search
CPC .................. G06T 7/10; G06T 2200/24; G06T 2207/10081; G06T 2207/10116; G06T 2207/20092; G06T 2207/30004
See application file for complete search history.

(56) References Cited

U.S. PATENT DOCUMENTS

| | | | |
|---|---|---|---|
| 2009/0262896 A1* | 10/2009 | Maschke | A61B 6/467 378/98 |
| 2012/0230570 A1 | 9/2012 | Zheng | |
| 2014/0153690 A1* | 6/2014 | Claus | A61B 6/025 378/9 |

OTHER PUBLICATIONS

"Intuitive 3D Catheter Guidance" Philips, 2012.
Liu, Baodong et al "Image Reconstruction from Limited Angle Projections Collected by Multisource Interior X-Ray Imaging Systems", Physics in Medicine Biology, vol. 56, 2011, pp. 6337-6357/.
Toshiba Leading Innovation, Fluoroscopy System X-Ray Radiology System/for fluoroscopy/for Cardiac Fluoroscopy/C-Arm, Infinix CF-i/BP Toshiba Medical Systems, 2014.

* cited by examiner

ADAPTIVE SEGMENTATION FOR ROTATIONAL C-ARM COMPUTED TOMOGRAPHY WITH A REDUCED ANGULAR RANGE

CROSS-REFERENCE TO PRIOR APPLICATIONS

This application is the U.S. National Phase application under 35 U.S.C. § 371 of International Application No. PCT/EP2016/050131, filed on Jan. 6, 2016, which claims the benefit of European Patent Application No. 15151099.7, filed on Jan. 14, 2015. These applications are hereby incorporated by reference herein.

FIELD OF THE INVENTION

The present invention relates to the field of C-arm X-ray imaging. In particular, the present invention relates to a system and a method for adaptive segmentation.

BACKGROUND OF THE INVENTION

C-arm computed tomography X-ray imaging, C-arm CT, is receiving increased interest for complex cardiac interventions such as, for instance, Transcatheter Aortic Valve Implantation, TAVI. It allows for a three-dimensional, 3D, assessment of aortic anatomy in the catheterization laboratory, abbreviated Cathlab, providing options for treatment planning and interventional guidance.

However, the requirements for treatment planning and interventional guidance differ considerably. In a treatment planning context, a high accuracy of the segmentation (and, therefore, a high image quality) is required in order to facilitate e.g. the selection of the correct size TAVI device. Contrary, during an intervention, the requirements regarding the segmentation accuracy are lower, and workflow aspects become increasingly more and more important.

EP 2 485 646 B1 describes an automatic C-arm positioned at viewing angles for structural heart disease treatment. A method for positioning an X-ray image acquisition device is provided as well as a medical viewing system comprising an X-ray image acquisition device and adapted for automatically positioning the X-ray image acquisition device.

U.S. Pat. No. 8,111,894 B2 describes a system and a method for acquiring image data, which can be used in order to perform a scanning of an object under examination. The C-arm CT system is described to be used for examination of an object of interest. The C-arm CT system as therein described comprises an X-ray tube adapted for generating X-rays and an X-ray detection unit to acquire a set of C-arm CT slices.

SUMMARY OF THE INVENTION

There may be a need to improve devices and methods in the field of C-arm based computed tomography X-ray imaging.

This is met by the subject-matter of the independent claims. Further exemplary embodiments are evident from the dependent claims and the following description.

A first aspect of the present invention relates to a medical imaging system comprising a C-arm imaging device for acquiring X-ray images over an angular range. The system comprises a configurator, which is configured to determine, with respect to the full angular range (i.e. the maximum angular range) of the C-arm, an adapted angular range in accordance with an operation mode of the system. The configurator also determines a segmentation parameter based on the adapted angular range. Still further, the system comprises a segmentator, which is configured to generate a segmentation model based on the acquired images using the determined segmentation parameter.

The term "segmentation model" as used by the present invention may refer to a specific instance of a segmentation technique. The segmentation technique may be performed in determining structures of interest or organs which may have a repetitive form of geometry. Therefore, the segmentator may search for a probabilistic model towards reflecting the variation of the shape of the organ and then, when segmenting an image, the segmentator may impose constraints using the model.

The present invention advantageously provides a system for adaptive segmentation that adapts the parameterization, e.g. model features, of the segmentation technique depending on the adapted angular range, and offers corresponding image processing functionality. The determined segmentation parameter may be used as an input to the segmentation technique or to the generated segmentation model.

In operation, the C-arm device performs a rotational scan for acquiring images over the adapted angular range. Advantageously, a 3D reconstruction or partial 3D reconstruction is carried out, taking the acquired images as an input. The segmentator may then operate on the (partial) 3D reconstruction to carry out an optimal segmentation based on the determined segmentation parameter.

The present invention advantageously provides a segmentation technique for C-arm CT (also called "XperCT") or reduced range C-arm CT that can be dynamically adapted to different acquisitions ranges in order to optimize the segmentation for a particular application. In contrast to existing solutions, the present invention advantageously allows addressing the varying requirements of, for example, TAVI use cases such as pretreatment planning and guidance during interventional procedure.

Since the image quality of certain acquisition might not allow for accurate measurements (e.g. due to artifacts which result from a reduction of the angular range), the present invention advantageously provides a coupling between the image processing functionality, which is determined by the acquisition protocol or the segmentation parameters and the adapted or reduced angular range.

Preferably, the system further comprises a display device configured to display the generated segmentation model.

According to a further aspect of the present invention, a method for adaptive segmentation is provided, the method comprising the steps of:

a) determining an adapted angular range with respect to an operation mode of the system and determining a segmentation parameter based on the adapted angular range by a configurator;

b) acquiring images within the adapted angular range by an imaging sensor processor; and c) generating a segmentation model based on the acquired images using the determined segmentation parameter by a segmentator.

According to an exemplary embodiment of the present invention, the system may further comprise a configurable user interface, which is configured to selectively display functionality used for controlling the system based on the adapted angular range. That is, certain functionality of the user interface may be altered, enabled and/or disabled by an interface configurator, in dependence of the adapted angular range. This advantageously provides a coupling between the image processing functionality and the adapted angular range. For example, the use of certain image measurement functions in the user interface could be permitted or denied by means of the interface configurator.

According to an exemplary embodiment of the present invention, the system may further comprise an image analyzer, which is configured to identify a landmark on the acquired images based on the generated segmentation model. The landmark may be identified using the segmentation model. The landmark may be derived from the image analyzer which could also use the imaging parameters or the segmentation parameters.

According to an exemplary embodiment of the present invention, the image analyzer may alternatively or additionally be configured to perform a measurement on the acquired images based on the generated segmentation model. For example, the measurement may be a photogrammetric measurement, i.e. making measurements from the acquired images, especially for recovering the lengths or distances of structures or positions of surfaces or bodies. This advantageously improves the accuracy of the photogrammetric measurement and/or of the landmark identification. For instance, the photogrammetric measurement may be a diameter or length measurement of an aorta or of an artery or of a vein or of a blood vessel in the human body.

According to an exemplary embodiment of the present invention, the configurator is configured to determine an imaging parameter with respect to an operation mode of the system. This advantageously improves the quality of the acquired images.

According to an exemplary embodiment of the present invention, the configurator is configured to determine the imaging parameter in form of an X-ray voltage used by the imaging sensor to acquire the images; or in form of an acquisition speed used by the imaging sensor; or in form of a determined quantity of the acquired images used by the imaging sensor. This advantageously also improves the quality of the acquired images.

According to an exemplary embodiment of the present invention, the configurator is configured to determine: the adapted angular range or an imaging parameter with respect to a treatment planning mode; or to a pre-interventional examination mode; or to an intra-interventional examination mode; or to a post-interventional examination mode as the operation mode of the system. In other words, at least one or both, i.e. the adapted angular range and/or the imaging parameter may be determined based on what sort of operation mode of the system is currently used, namely, a treatment planning mode; or a pre-interventional examination mode; or an intra-interventional examination mode; a post-interventional examination mode.

According to an exemplary embodiment of the present invention, the configurator is configured to determine the adapted angular range to up to 180° or to up to 140° or to up to 110° or to up to 90°. This advantageously allows reducing an impairment of the user performing an interventional procedure due to the closeness or the arrangement of tools, for instance, the C-arm and further tools or devices.

According to an exemplary embodiment of the present invention, the segmentator is configured to generate the segmentation model with respect to the adapted angular range. This advantageously improves the quality of the generated segmentation model.

The methods, systems and devices described herein may be implemented as software in a Digital Signal Processor, DSP, in a micro-controller or in any other side-processor or as hardware circuit within an application specific integrated circuit, ASIC or in a field-programmable gate array which is an integrated circuit designed to be configured by a customer or a designer after manufacturing.

The present invention can be implemented in digital electronic circuitry, or in computer hardware, firmware, software, or in combinations thereof, e.g. in available hardware of conventional medical devices or medical imaging device or in new hardware dedicated for processing the methods described herein.

These and other aspects of the present invention will become apparent from and be elucidated with reference to the embodiments described hereinafter. A more complete appreciation of the present invention and the attendant advantages thereof will be more clearly understood with reference to the following schematic drawings.

BRIEF DESCRIPTION OF THE DRAWINGS

A more complete appreciation of the present invention and the attendant advantages thereof will be more clearly understood with reference to the following schematic drawings, which are not to scale, wherein.

DETAILED DESCRIPTION OF EMBODIMENTS

Figure 2:
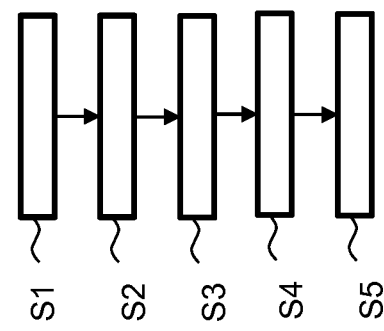
FIG. 2 shows a schematic diagram of a flowchart diagram of a method for adaptive segmentation according to an exemplary embodiment of the present invention.

The illustration in the drawings is purely schematic and does not intend to provide scaling relations or size information. In different drawings or figures, similar or identical elements are provided with the same reference numerals. Generally, identical parts, units, entities or steps are provided with the same reference symbols in the description.

The term "segmentation" as used by the present invention may refer to a process of partitioning or dividing a digital image or a structure as present in the digital image or as present in multiple images of series of acquired images into multiple segments. By the segmentation, a further image processing or image analysis may be improved.

Figure 1:
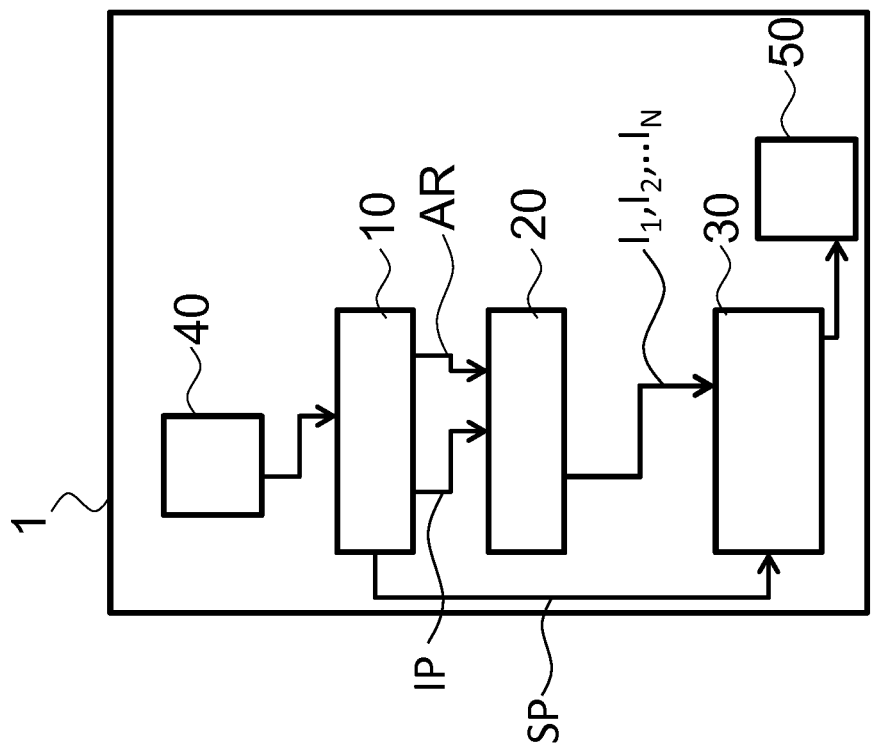
FIG. 1 shows a schematic diagram of a system for adaptive segmentation according to an exemplary embodiment of the present invention.

FIG. 1 shows a schematic diagram a system for adaptive segmentation according to an exemplary embodiment of the present invention.

A medical imaging system 1 according to the invention may comprise a configurator 10, a C-arm imaging device 20, and a segmentator 30.

The configurator 10 may be configured to determine an adapted angular range AR with respect to an operation mode of the system 1 and may be configured to determine a segmentation parameter SP based on the adapted angular range AR.

The imaging device 20 is a C-arm type X-ray imaging device as known per se in the art. The imaging device comprises an X-ray source and an X-ray detector mounted on a C-arm support; the detector is configured to detect and convert X-rays into electronic signals.

The segmentator 30 may be configured to generate a segmentation model based on the acquired images $I_1, \ldots, I_N$ using the determined segmentation parameter SP. Executing or performing the generated segmentation model may create an explicit segmentation step, wherein the segmentation parameters SP are used as input for the segmentation model.

The segmentation model may be used as an implementation of a segmentation technique like model based segmentation which can generate, for instance, an aorta segmentation.

A segmentation parameter SP may be a specific setting or an input for the segmentation technique or the segmentation model.

The segmentator 30 may be a configuration engine which generates a segmentation model based on the segmentation parameters SP.

The configurator 10 and/or the segmentator 30 may be a soft- or hardware module or a soft- or hardware functional unit that comprises a separated functionality. In other words, the configurator 10 and/or the segmentator 30 may be independent, interchangeable modules, e.g. hard- or software entities that may be distributed over a data processing system or a data processing computer network. Preferably, the configurator 10 and segmentator 30 are provided as part of a dedicated imaging workstation.

According to an exemplary embodiment of the present invention, the acquired images $I_1, \ldots, I_N$ may be combined with model-based segmentation to allow for automatic landmark identification (e.g. coronary ostia) and generation of measurements (e.g. annulus diameter). The requirements for treatment planning and interventional guidance differ considerably. In planning, a high quality and a high accuracy of the segmentation result is desirable. On the other hand, during an intervention, workflow aspects are more important. For this purpose, a reduced angular range may be used for acquiring the images $I_1, \ldots, I_N$ that may be accurate enough, while avoiding the need for a full rotation scan with the C-arm.

According to an exemplary embodiment of the present invention, the parameterization of the segmentation technique may be adapted depending on the available angular range. Thus, the segmentation may be adapted to different acquisition ranges.

According to an exemplary embodiment of the present invention, the system 1 may further comprise an interface configurator 40, which is configured to alter, or to enable, or to disable a functionality as displayed by the interface configurator 40 used for controlling the system 1 based on the determined and adapted angular range AR.

According to an exemplary embodiment of the present invention, the system 1 may further comprise an image analyzer 50, which is configured to identify a landmark on the acquired images $I_1, \ldots, I_N$ based on the generated segmentation model and/or which is configured to perform a photogrammetric measurement on the acquired images $I_1, \ldots, I_N$ based on the generated segmentation model.

According to an exemplary embodiment of the present invention, the configurator 10 may be configured to determine an imaging parameter IP with respect to an operation mode of the system 1. For instance, the operation mode may be a mode for treatment planning in pre- or post-interventional procedures or the operation mode may be a mode during an interventional procedure, for instance, a mode related to any kind of interventional guidance.

FIG. 2 shows a schematic diagram of a flowchart diagram of a method for adaptive segmentation according to an exemplary embodiment of the present invention.

As a first step of the method, determining S1 an adapted angular range AR with respect to an operation mode of the system 1 is conducted by a configurator 10 as well as determining a segmentation parameter SP based on the adapted angular range AR by a configurator 10 is conducted.

As a second step of the method, acquiring S2 images $I_1, \ldots, I_N$ within the adapted angular range AR is conducted by an imaging sensor processor 20.

As a third step of the method, generating S3 a segmentation model based on the acquired images $I_1, \ldots, I_N$ using the determined segmentation parameter SP is conducted by a segmentator 30.

According to an exemplary embodiment of the present invention, a further step S4 may be conducted comprising an altering or an enabling or a disabling of a functionality as displayed by the interface configurator 40 based on the adapted angular range AR. The modification may be performed by an interface configurator 40.

According to an exemplary embodiment of the present invention, a further step S5 may be conducted comprising an identifying of a landmark on the acquired images based on the generated segmentation model by an image analyzer 60.

According to an exemplary embodiment of the present invention, the step S5 may also comprise performing a measurement on the acquired images $I_1, \ldots, I_N$ based on the generated segmentation model.

Figure 3:
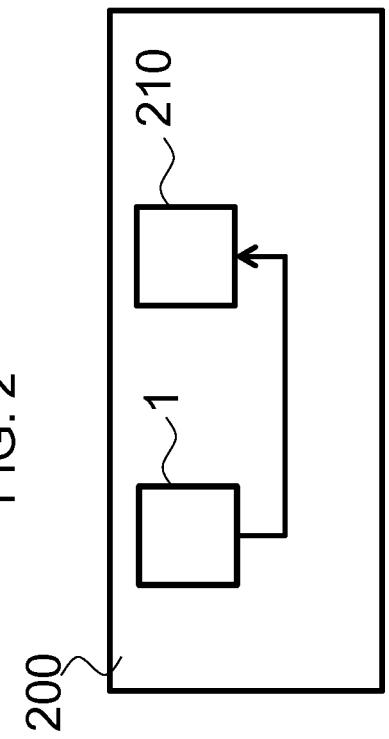
FIG. 3 shows a schematic diagram of a medical imaging device according to an exemplary embodiment of the present invention.

FIG. 3 shows a schematic diagram of a medical imaging device according to an exemplary embodiment of the present invention.

According to an exemplary embodiment of the present invention, a medical imaging system 200 may comprise a display device 210 in addition to a system 1 as previously described, wherein the display device 210 is configured to display the generated segmentation model.

Figure 4:
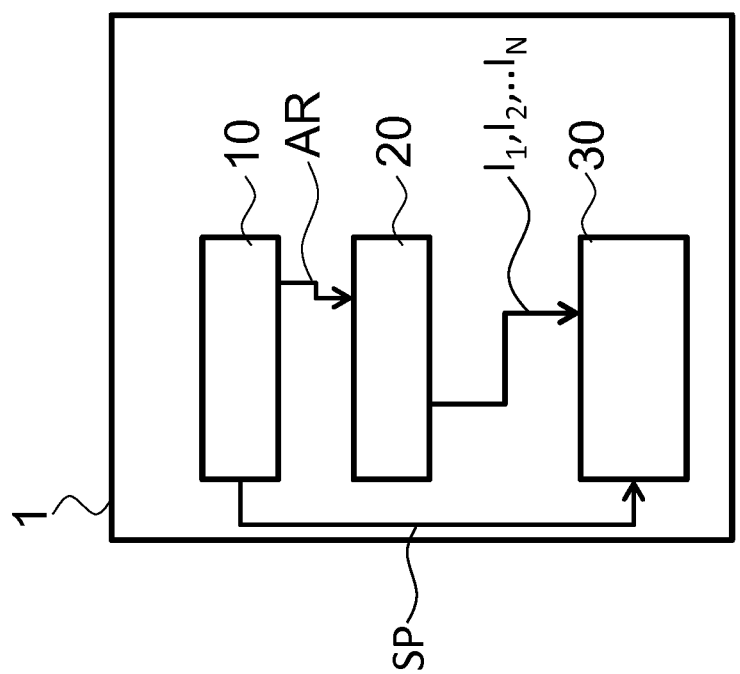
FIG. 4 shows a schematic diagram of a system for adaptive segmentation according to an exemplary embodiment of the present invention.

FIG. 4 shows a schematic diagram of a medical imaging system according to an exemplary embodiment of the present invention.

The system 1 may comprise a configurator 10, a C-arm imaging device 20, and a segmentator 30.

The configurator 10 may be configured to determine an adapted angular range AR with respect to an operation mode of the system 1 and may be configured to determine a segmentation parameter SP based on the adapted angular range AR.

The imaging sensor 20 may be configured to acquire images $I_1, \ldots, I_N$ within the adapted angular range AR.

The segmentator 30 may be configured to generate a segmentation model based on the acquired images $I_1, \ldots, I_N$ using the determined segmentation parameter SP.

Figure 5:
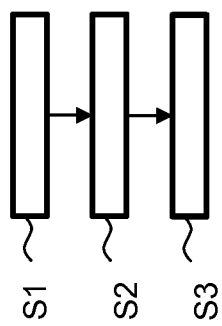
FIG. 5 shows a schematic diagram of a flowchart diagram of a method for adaptive segmentation according to an exemplary embodiment of the present invention.

FIG. 5 shows a schematic diagram of a flowchart diagram of a method for adaptive segmentation according to an exemplary embodiment of the present invention.

Initially, determining S1 an adapted angular range AR with respect to an operation mode of the system 1 is conducted by a configurator 10 as well as determining a segmentation parameter SP based on the adapted angular range AR is conducted by a configurator 10.

Subsequently, acquiring S2 images $I_1, \ldots, I_N$ within the adapted angular range AR is conducted by an imaging sensor processor 20.

Finally, generating S3 a segmentation model based on the acquired images $I_1, \ldots, I_N$ using the determined segmentation parameter SP is conducted by a segmentator 30.

Figure 6:
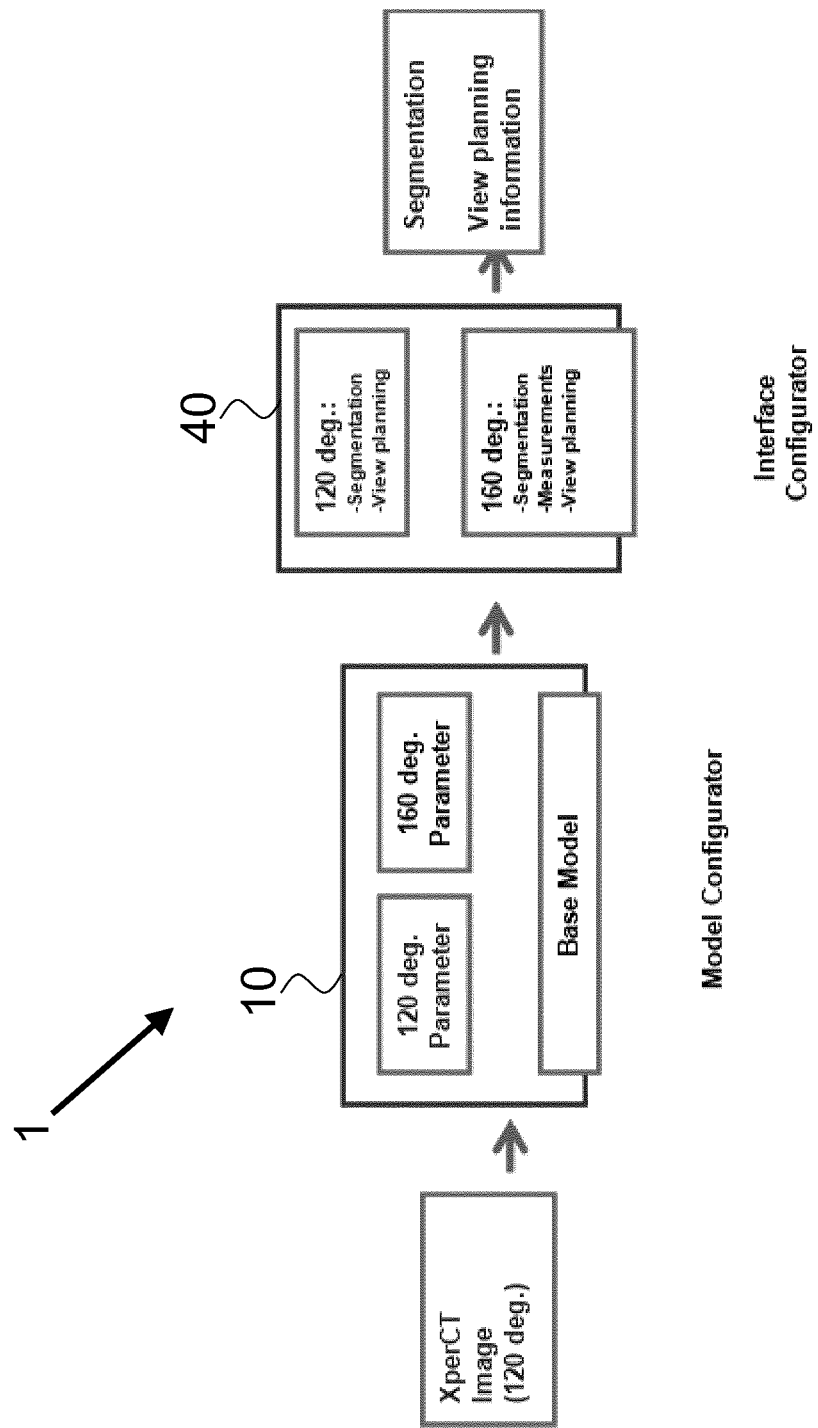
FIG. 6 shows a schematic diagram a system for adaptive segmentation according to an exemplary embodiment of the present invention.

FIG. 6 shows a schematic diagram a system for adaptive segmentation according to an exemplary embodiment of the present invention.

According to an exemplary embodiment of the present invention, for the C-arm CT for TAVI scenario, the proposed invention can be implemented in terms of a configurable segmentation technique, and an adaptive user interface, as depicted in FIG. 6.

According to an exemplary embodiment of the present invention, using the adapted angular range of the rotational scan and other imaging parameters IP, a model configurator in terms of the configurator 10 can be employed to adjust properties in form of segmentation parameters SP of the segmentation model in order to optimize the quality of the outcome. For model-based segmentation techniques, this may include for instance the boundary detectors, or the internal energy (which controls the trade-off between accuracy and robustness).

According to an exemplary embodiment of the present invention, while the image quality of a full range C-arm CT acquisition can be available for planning purposes, this may be not fulfilled for short range acquisitions which are optimized with respect to workflow aspects. The short range acquisitions may be defined by the adapted angular range AR. Therefore, depending on the image quality and/or depending on imaging parameters IP, different corresponding functionality should be or should be not available to the user. In other words, the functionality may be customized with respect to the imaging parameters IP.

According to an exemplary embodiment of the present invention, in FIG. 6, an intended segmentation framework is shown providing adapted model parameters and selected image processing functionality. Using for instance a 120 degree reconstruction, the configurator 10 in form of a model configurator may select the proper parameterization in terms of segmentation parameter SP of the segmentation model in order to optimize the segmentation as performed by the generated segmentation model. While the image quality may be sufficient for view planning purposes, for example measurement functionality may be disabled by the interface configurator 40.

According to an exemplary embodiment of the present invention, the workflow for two common use cases in the TAVI context could look as follows:

If a pre-interventional C-arm CT dataset of sufficient quality (and the necessary measurements) is available, a physician may be mainly interested in view planning. Therefore, he may select a reduced angular scan with a minimal impact on the workflow.

In this context the configurator 10 may be configured to determine the optimal model parameters or segmentation parameter SP prior to the segmentation. Since in a reduced angular scan with an adapted angular range AR detailed measurements are not feasible, only functionality for view planning will be available for the user.

According to an exemplary embodiment of the present invention, in an emergency situation a user might have to do the planning directly in the Cathlab. Therefore, the user could select a high high in terms of maximal available quality full range scan, for instance over an angular range of 160°. Again the configurator 10 of the system 1 would choose an optimal parameter set, while measurement functionality would be activated.

According to an exemplary embodiment of the present invention, the system 1 may be configured to be used to cope with cancelled rotational acquisitions, either because the C-arm body guard or the operator stopped the acquisition. The available angular range of the projection data may be analyzed and may be mapped to the parameter model trained with the most similar angular range.

According to an exemplary embodiment of the present invention, the system 1 may be configured to be used to support so-called 'free-hand' acquisitions, where the angular range is not determined beforehand but chosen during acquisition by the operator.

Visual feedback may be given to the operator in real-time using the interface configurator 40, for instance, a red light may be displayed via the display device 210 as long as the angular range is below a certain minimum e.g. 120°. The certain minimum may be determined by the operation mode or may be defined by a threshold value determined for an application of the system 1.

According to an exemplary embodiment of the present invention, a yellow light may be displayed via the display device 210 when the range is sufficient for view planning, for instance 120° to 150° and a green light may be displayed via the display device 210 afterwards when the range is sufficient for measurement applications.

Figure 7:
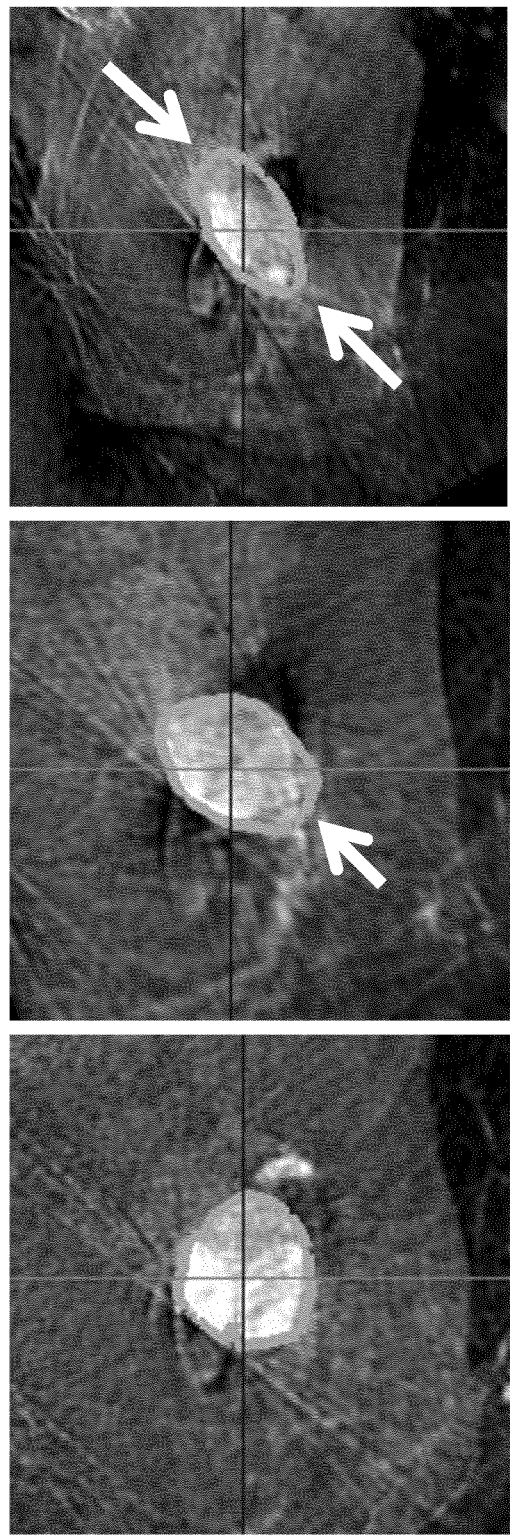
FIG. 7 shows a schematic diagram of results from a model-based segmentation of the aorta using a 160-degree, a 140-degree, and a 110-degree reconstruction for explaining the present invention.

FIG. 7 shows a schematic diagram of results from a model-based segmentation of the aorta using a 160-degree, a 140-degree, and a 110-degree reconstruction for explaining the present invention, depicted from left to right in FIG. 7.

For illustration purposes a cut through the same topological region of the model mesh for different reconstructions is depicted in FIG. 7.

According to an exemplary embodiment of the present invention, with a reduction of the adapted angular range AR and an increase of imaging artifacts, the segmentation as performed by the segmentator 30 may become distorted when comparing the 160-degree, the 140-degree, and the 110-degree reconstruction as indicated by the white arrows, showing a decreasing measurement accuracy considerably with decreasing angular range.

It has to be noted that embodiments of the present invention are described with reference to different subject-matters. In particular, some embodiments are described with reference to method type claims whereas other embodiments are described with reference to device type claims.

However, a person skilled in the art will gather from the above and the foregoing description that, unless otherwise notified, in addition to any combination of features belonging to one type of the subject-matter also any combination between features relating to different subject-matters is considered to be disclosed with this application.

However, all features can be combined providing synergetic effects that are more than the simple summation of these features.

While the present invention has been illustrated and described in detail in the drawings and the foregoing description, such illustration and description are to be considered illustrative or exemplary and not restrictive; the present invention is not limited to the disclosed embodiments. Other variations to the disclosed embodiments can be understood and effected by those skilled in the art and practicing the claimed invention, from a study of the drawings, the disclosure, and the appended claims.

In the claims, the word "comprising" does not exclude other elements or steps, and the indefinite article "a" or "an" does not exclude a plurality. A single processor or controller or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. A medical imaging system comprising:
   a C-arm imaging device comprising a C-arm, the C-arm imaging device being configured to acquire X-ray images ($I_1, \ldots, I_N$) over an angular range;
   a configurator circuit configured to determine: i) an adapted angular range in accordance with an operation mode of the medical imaging system, the adapted angular range being adapted with respect to a full angular range of the C-arm; and ii) a segmentation parameter directly based on the adapted angular range; and
   a segmentator circuit configured to generate a segmentation model based on the acquired X-ray images ($I_1, \ldots, I_N$) using the determined segmentation parameter.

2. The medical imaging system according to claim 1, further comprising a configurable user interface, which is configured to selectively display functionality used for controlling the medical imaging system based on the adapted angular range.

3. The medical imaging system according to claim 1, further comprising an image analyzer circuit configured to identify a landmark on the acquired X-ray images ($I_1, \ldots, I_N$) based on the generated segmentation model.

4. The medical imaging system according to claim 1, further comprising an image analyzer circuit configured to perform a measurement on the acquired X-ray images ($I_1, \ldots, I_N$) based on the generated segmentation model.

5. The medical imaging system according to claim 1, wherein the configurator circuit is configured to determine an imaging parameter with respect to an operation mode of the medical imaging system.

6. The medical imaging system according to claim 5, wherein the configurator circuit is configured to determine the imaging parameter in form of an X-ray voltage used by the C-arm imaging device to acquire the X-ray images ($I_1, \ldots, I_N$); or in form of an acquisition speed used by the C-arm imaging device; or in form of a determined quantity of the acquired X-ray images ($I_1, \ldots, I_N$) used by the imaging device.

7. The medical imaging system according to claim 5, wherein the configurator circuit is configured to determine:
   the adapted angular range or the imaging parameter with respect to
   a treatment planning mode; or to
   a pre-interventional examination mode; or to
   an intra-interventional examination mode; or to
   a post-interventional examination mode
   as the operation mode of the medical imaging system.

8. The medical imaging system according to claim 7, wherein the configurator circuit is configured to determine the adapted angular range to up to 180°, or to up to 140°, or to up to 110°, or to up to 90°.

9. The medical imaging system according to claim 7, wherein the segmentator circuit is configured to generate the segmentation model with respect to the adapted angular range.

10. The medical imaging system according to claim 1, further comprising a display device configured to display the generated segmentation model.

11. A method for adaptive segmentation, the method comprising:
    a) determining, with respect to a full angular range of a C-arm imaging device, an adapted angular range in accordance with an operation mode of an X-ray imaging system and determining a segmentation parameter directly based on the adapted angular range by a configurator;
    b) acquiring images ($I_1, \ldots, I_N$) within the adapted angular range by the C-arm imaging device; and
    c) generating a segmentation model based on the acquired X-ray images ($I_1, \ldots, I_N$) using the determined segmentation parameter by a segmentator.

12. The method according to claim 11, further comprising altering, enabling, or disabling functionality in a user interface based on the adapted angular range by an interface configurator.

13. The method according to claim 11, further comprising identifying a landmark on the acquired images based on the generated segmentation model by an image analyzer.

14. The method according to claim 11, further comprising performing a photogrammetric measurement on the acquired X-ray images ($I_1, \ldots, I_N$) based on the generated segmentation model.

15. The method according to claim 11, further comprising determining an imaging parameter with respect to an operation mode of the X-ray imaging system by the configurator.

* * * * *